United States Patent [19]

Shaw et al.

[11] 4,423,256

[45] Dec. 27, 1983

[54] RECOVERY OF SECONDARY ALKANOLS

[75] Inventors: Paul V. Shaw; Larry W. Payne, both of Houston, Tex.; Charles E. Sanborn, Walnut Creek, Calif.; Eugene F. Lutz, Houston, Tex.

[73] Assignee: Shell Oil Company, Houston, Tex.

[21] Appl. No.: 435,429

[22] Filed: Oct. 20, 1982

[51] Int. Cl.³ .............................................. C07C 29/06
[52] U.S. Cl. .................................... 568/886; 568/888
[58] Field of Search ............................. 568/886, 888

[56] References Cited

U.S. PATENT DOCUMENTS

| | | | |
|---|---|---|---|
| 1,844,209 | 2/1932 | Davis et al. | 568/888 |
| 1,955,416 | 4/1934 | Engs et al. | 568/888 |
| 2,467,846 | 4/1949 | Mottern et al. | 568/886 |

Primary Examiner—J. E. Evans

[57] ABSTRACT

An improved method for recovery of product alkanol and reactant olefin from a reaction mixture obtained via the sulfation and hydrolysis of $C_6$ to $C_{20}$ olefins, which comprise steps for a limited first evaporation of the reaction mixture under alkaline conditions to obtain an alkanol and olefin rich vapor and a liquid containing by-products of the sulfation and hydrolysis reactions, acid wash of the resulting liquid, and a second evaporation of alkanol and olefin from the washed liquid under acidic conditions. In addition to accomplishing separation of alkanol and olefin, the invention enhances selective utilization of $C_6$ to $C_{20}$ olefins for production of $C_6$ to $C_{20}$ alkanols.

10 Claims, 1 Drawing Figure

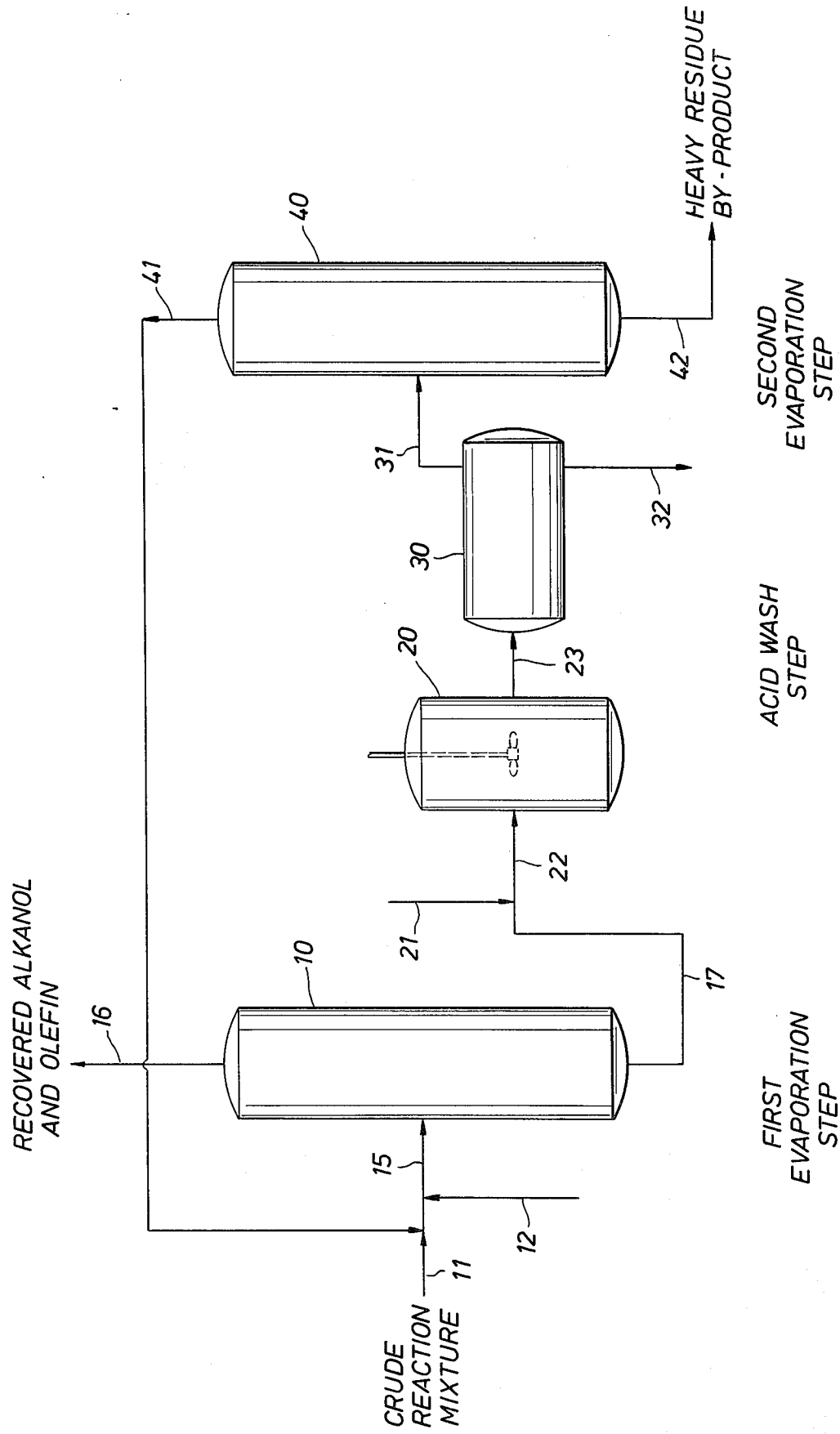

RECOVERY OF SECONDARY ALKANOLS

BACKGROUND OF THE INVENTION

This invention relates to an improvement in processes for the preparation of higher secondary and tertiary alkanols from olefins via sulfation and hydrolysis reactions. More particularly, this invention relates to a method for the enhanced recovery of alkanols in high selectivity from the crude reaction mixture of such a process.

The hydration of higher ($C_6$ to $C_{20}$) olefins to alkanols of corresponding carbon number is known to be accomplished by a process in which the olefins undergo sulfation by reaction with concentrated sulfuric acid to yield monoalkylsulfuric acids (alkyl sulfate esters) which are then hydrolyzed to the desired alkanols. Markovnikov addition yields secondary or tertiary alkanols. $C_6$ to $C_{20}$ secondary and tertiary alkanols are commercial materials having established utility in a variety of applications, for instance, as plasticizers and as intermediates in the synthesis of surfactants and lubricants.

A major limitation on the efficiency of alkanol preparation in this manner relates to the formation during the sulfation and hydrolysis reactions of a number of by-product compounds. For instance, the crude reaction mixture obtained following hydrolysis contains, in addition to alkanol and olefin, a substantial quantity of such by-products as olefin dimers and polymers, dialkylethers, alkyl sulfates, dialkyl sulfates, and alkyl sulfonates. Overall, by-product make in a process having an acceptable rate and conversion of olefin to alkanol typically accounts for a processing loss, measured in terms of utilization of olefin starting material, that is on the order of 3 to 15 percent. It is an object of this invention to provide an improvement in alkanol preparation processes which results in a low net production of such by-products. It is a further object of this invention to provide improvement in alkanol preparation processes which results both in a low net production of by-products and in an acceptably high yield of alkanol.

SUMMARY OF THE INVENTION

A relatively simple and cost effective means has now been found to improve selectivity in a process for the synthesis of higher alkanols from olefins via sulfation and hydrolysis reactions.

The improvement of the invention does not center upon these synthesis reactions per se, but instead upon downstream process steps for separation of the resulting product mixture. For purposes of the invention, alkanol and olefin are recovered from the product mixture in multiple evaporation steps. When conducted under specified conditions and accompanied by an aqueous acid wash step, these evaporations selectively promote decomposition of undesirable by-products of the sulfation and hydrolysis reactions to recoverable alkanol and olefin. Of particular importance is the practice of a first evaporation step conducted under alkaline condition and under restriction upon the extent of alkanol separation, followed by an aqueous acid wash of the first evaporation bottoms liquid, and then by a second, essentially complete evaporation of alkanol from this washed liquid under acidic conditions. In preferred embodiments, conditions of the evaporation steps limit the reversion of alcohol to olefin, which typically accompanies by-product decomposition during the evaporations, insuring minimum sacrifice in overall process yields.

The invention is of particular advantage in that it does not rely upon the sulfation and hydrolysis reaction steps for the indicated benefits. Under the improved process now provided, the steps of the invention as well as the synthesis reaction steps by which they are preceeded can be independently optimized for overall process performance. Still, because of its intended application in the course of process separations steps otherwise useful for product recovery, the invention is particularly cost effective and readily implemented.

Accordingly, as an improvement upon the process for the preparation of alkanols which comprises sulfating a $C_6$ to $C_{20}$ olefin starting material by reaction with concentrated sulfuric acid, hydrolyzing the resulting alkylsulfuric acids to obtain a crude reaction mixture containing $C_6$ to $C_{20}$ alkanol, $C_6$ to $C_{20}$ olefin and heavy by-products, and separating the alkanol and olefin in the reaction mixture from the heavy by-product therein, the invention may be summarily described as comprising steps for:

(a) in a first evaporation step, evaporating the crude reaction mixture under alkaline pH, withdrawing an alkanol and olefin rich first evaporation overhead vapor containing between about 80 and 98 percent by weight of the alkanol present in the crude reaction mixture and withdrawing a heavy by-product rich first evaporation bottoms liquid, (b) in an acid wash step, contacting the first evaporation bottoms liquid with an aqueous acid contact solution and separating the resulting mixture into a washed organic contact phase and an aqueous contact effluent phase, under the provision that the acid content of the aqueous acid contact solution is sufficient to produce an aqueous contact effluent phase having a pH of less than about 1.5, (c) in a second evaporation step, evaporating the washed organic contact phase under acid pH, and withdrawing a second evaporation overhead vapor and a second evaporation bottoms liquid, said second evaporation overhead vapor containing a combined quantity by mole of alkanol and olefin in excess of that present in the washed organic contact phase.

Overall, these process steps provide enhanced selectivity, on the basis of olefin utilization, through a net decrease in heavy by-product and a corresponding net increase in the total recovery from the crude reaction mixture of alkanol product and olefin starting material.

DESCRIPTION OF THE DRAWING

Reference is made to the attached drawing which in a single FIGURE illustrates a schematic flow diagram of the process steps of a preferred embodiment of the present invention. It is to be understood that the drawing is of simplified form and does not purport to show instrumentation, valving, fluid pumping, heat exchange, and other processing details which are matters of implementation obvious to those skilled in the chemical processing arts. The embodiment shown is a continous process, although batch operation under the invention is also contemplated.

In the process depicted, a crude alkanol reaction mixture, designated 11, derived from $C_6$ to $C_{20}$ olefins via sulfation and hydrolysis reactions is introduced for the first evaporation step of the invention into evaporator 10. The crude reaction mixture is typically acidic and contains, for example, about 70 to 80 percent by weight (%w) alkanol, 12 to 20%w olefin and 5 to 10%w heavy by-product. A quantity of base (e.g., caustic soda) is also introduced together with the reaction mixture into the first evaporation step to provide an alkaline evaporation liquid. In the process shown, base 12 is mixed with reaction mixture 11 upstream of evaporator 10. Optionally, but preferably, a recycle stream 41, containing alkanol and olefin evaporated in the second evaporation step, is also mixed with stream 11. The resulting mixture 15 is heated (by means not shown) to separate a first evaporation overhead vapor, which is withdrawn from the evaporator 10 as stream 16, and a first evaporation bottoms liquid, which is withdrawn as stream 17. For the case shown in which stream 41 is recycled to the first evaporation step, stream 16 contains a combined quantity by mole of olefin and alkanol in excess of that in stream 11. Without such recycle, streams 16 and 41 together contain a greater quantity by mole of olefin and alkanol than stream 11.

In the second process step, the alkaline first evaporation bottoms liquid 17 is subjected to an aqueous acid wash by contact with acid and extraction with water. Here, an aqueous acid solution 21 (e.g., 3%w $H_2SO_4$ in water) is contacted with stream 17 under agitation in mixing vessel 20, and the resulting stream 23 is phase separated in settling vessel 30. An aqueous contact effluent phase 32 is withdrawn from the wash step and from the process as shown. Sufficient acid is introduced via stream 21 to provide a pH in this aqueous contact effluent that is no greater than about 1.5.

The wash step yields a washed organic contact phase 31 which is withdrawn from vessel 30 and introduced for purposes of the second evaporation step into evaporator 40. Stream 31 is subjected to evaporation under acidic conditions and at a temperature of at least about 400° F. in evaporator 40 to produce a second evaporation bottoms liquid 42 and a second evaporation overhead vapor 41. Vapor 41 contains a combined quantity, by mole, of alkanol and olfein which is in excess of that present in the washed organic contact phase 31, the result of essentially complete evaporation of alkanol and olefin in evaporator 40 and further the result of decomposition of heavy by-product promoted by the acidity and temperature of evaporation. As a result of such decomposition, the quantity of residual heavy by-product withdrawn in bottoms liquid 42 is less than that contained in stream 31, and likewise less than that in stream 11. Also, giving account to the possibility that some quantity of heavy by-product may be carried overhead in the second evaporation, the combined quantity of such by-product in both of stream 41 and 42 is less than that in stream 31 (or in stream 11). Alkanol and olefin rich stream 41 may be taken from the process, but is preferably recycled to the first evaporation step.

DESCRIPTION OF THE PREFERRED EMBODIMENTS

This invention is generally applicable to any process in which $C_6$ to $C_{20}$ alkanols are prepared by reaction of $C_6$ to $C_{20}$ mono-olefins with sulfuric acid, followed by hyrolysis of the resulting alkylsulfuric acids. Processing procedures and reaction conditions suitable for alkanol synthesis in this manner are well known in the art. Certain preferred procedures and conditions are described in the commonly-assigned copending application Ser. No. 363,175, filed Mar. 29, 1982, the relevant teachings of which are incorporated herein by reference. In addition, descriptions of particularly desirable aspects of olefin sulfation (also to be incorporated herein) are provided in U.S. Pat. Nos. 2,623,894, 2,640,070, and 4,226,797. For reasons relating to commercial utility of the product such a process is preferably applied to the manufacture of alkanols in the $C_8$ to $C_{18}$ range, more preferably the $C_9$ to $C_{16}$ range, and to alkanols having predominently linear (straight-chain) carbon structure. Olefin starting materials (and alkanol products) of mixed carbon numbers and molecular structures are very suitable for purposes of the invention.

There is obtained as the result of such sulfation and hydrolysis reactions a crude reaction mixture containing $C_6$ to $C_{20}$ alkanol, $C_6$ to $C_{20}$ olefin and heavy by-product compounds (higher molecular weight and higher boiling relative to alkanol and olefin), including, for example, olefin dimers and polymers, ethers, alkyl sulfuric and sulfonic acids and/or their sulfate and sulfonate salts. The presence of sulfuric acid as a reactant in the sulfation reaction and as a product of the hydrolysis reaction results in an acidic crude reaction mixture. (For purposes of describing this invention a process stream is described herein as acidic if a water extract, or hydrolysis product, thereof has a pH less than 7.0 and as alkaline if it has a pH greater than 7.0.)

For purposes of the invention, sulfation and hydrolysis reactions are followed, in the first evaporation step, by limited separation of the crude reaction mixture into alkanol and olefin rich vapor and heavy by-product rich liquid. It is necessary that this first evaporation be conducted under alkaline conditions, that is, the liquid undergoing evaporation must be of alkaline pH. In view of the acidity which is characteristic of the conventional crude reaction mixture, this requirement of alkalinity entails addition of a base to the mixture in a quantity in excess of that required to neutralize the acid components thereof. The choice of the base is not critical to the invention although the base and resulting salt should be relatively stable under the conditions of the first evaporation. Use of an inorganic base is preferred, particularly an alkali or alkaline earth metal hydroxide. The alkalinity of the liquid undergoing evaporation in this process step is preferably such that a water extract thereof one part water to one part evaporation liquid) has a pH of about 8 to 13, more preferably about 9 to 12.

Another important aspect of the first evaporation step is the degree of separation which it accomplishes between alkanol and olefin on the one hand and heavy by-product components on the other. As a rule, it is necessary that no more than about 98%w of the product $C_6$–$C_{20}$ alkanol entering this evaporation step be withdrawn with the overhead vapor and that at least about 2 percent of the alkanol introduced into the first evaporation step be withdrawn in the bottoms liquid together with substantially all of the heavy by-product. A lower limit for alkanol separation is also critical to the invention—recovery of the overhead vapor from the first evaporation of at least about 80%w of the product $C_4$ to $C_{20}$ alkanol entering in the feed to this step is necessary, while no more than 20%w of this alkanol is withdrawn in the bottoms liquid. Preference can be stated for operation under which at least about 85%w, but no more than about 96%w of the $C_6$ to $C_{20}$ alkanol in the crude mixture subjected to evaporation in the first evaporation step is taken overhead and at least 4 percent is withdrawn in the bottoms liquid, while evaporation of between about 90 and 95%w of this alkanol and withdrawal of at least 5%w in the bottoms is considered most preferred. Restrictions are placed upon the maximum degree of alkanol separation in this first evaporation step for reasons relating both to inhibiting decomposition and other undesirable reactions and to minimizing carry-over of heavy by-product components into the overhead vapor. A minimum degree of alkanol separation is also important to prevent unnecessary exposure of alkanols to conditions of the second evaporation step.

Equipment and procedures suitable for use in this first evaporation step of the invention, as well as for its second evaporation step, are well known to the processing arts. For purposes of describing this invention, evaporation is intended to encompass fractionation or distillation practices which similarly accomplish the indicated degree of separation of alkanol between overhead vapor and bottoms liquid.

As will be understood, processing parameters such as temperature and pressure for the first evaporation step are in large measure dependent upon the carbon number of the alkanol prepared and of the degree of separation of alkanol between the vapor and liquid withdrawn from the evaporation. However, a clear preference can be expressed for evaporation temperatures not exceeding 400° F. As a rule, temperature of the first evaporation is preferably greater than about 250° F., although lower temperatures can be suitably utilized, particularly in the case of alkanols of the lower carbon numbers. For alkanols of carbon number eight or more, first evaporation temperatures between about 300° and 380° F. are particularly preferred, while temperatures between about 320° and 370° F. are more preferred and temperatures between about 330° and 360° F. are considered most preferred. Consistent with the preferences expressed for processing temperature, pressure in the first evaporation step is preferably less than about 5 atmospheres when the alkanols have a carbon number equal to or greater than eight. Illustrative of typical pressures in the first evaporation step when conducted at 350° F. are 1500 mmHg for $C_8$ alkanol, 150 mmHg for $C_{11}$ alkanol, 20 mmHg for $C_{15}$ alkanol, and 2 mmHg for $C_{20}$ alkanol. When processing alkanols having carbon numbers of about 9 or greater, the first evaporation is preferably conducted under vacuum, that is, with provision for vapor withdrawal to maintain pressure at less than atmospheric, more preferably at a pressure less than about 100 mmHg, and most preferably at a pressure less than about 50 mmHg.

Following its withdrawal from the first evaporation step, but before the second evaporation step, the first evaporation bottoms liquid is subjected to the aqueous wash step of the invention. In order that the second evaporation be conducted under acidic conditions, it is necessary to add an acid to this alkaline bottoms liquid. It is further necessary to extract from the bottoms liquid water soluble materials, particularly inorganic salts, which would otherwise foul equipment and/or promote undesirable reactions at the elevated temperature of the subsequent evaporation. Preferably a dilute aqueous acid solution is brought into contact with the first evaporation bottoms liquid, under agitation to promote contact between aqueous and organic phases. Subsequent separation of the washed organic contact phase from the resulting aqueous acid and salt solution is conveniently accomplished by settling and phase separation. Temperature of the acid wash step is not critical. However, a temperature of at least about 120° F., preferably at least about 130° F., aids phase separation. The nature of the acid utilized is not critical, although both the acid and resulting salts should be stable under processing conditions. Strong inorganic acids are preferred, particularly sulfuric acid. The quantity of acid applied in the wash step is necessarily sufficient to result in a relatively low pH for the washed organic contact phase. In typical practice of the invention this requirement can be phrased in terms of a pH for the aqueous contact effluent phase, with which the organic phase is substantially in equilibrium, that is about equal to or less than 1.5. This specification on pH of the organic phase has been found necessary for purposes related both to the solubility between organic and aqueous wash phases and to the selective decomposition of heavy by-product in the subsequent evaporation. A pH of this aqueous effluent phase between about 0.0 and 1.0 is preferred, while a pH between about 0.1 and 0.7 is considered more preferred and a pH between about 0.3 and 0.5 most preferred. The quantity of water utilized in the wash step is not critical, although consideration should be given to a quantity which is sufficient to effectively extract salts and the like. Preference can generally be given to a volume of aqueous acid that is between about 0.2 and 10 times that of the bottoms liquid.

In the first evaporation step of the invention, evaporation of the crude reaction mixture accomplishes partial separation of alkanol and olefin therefrom under conditions (e.g., alkalinity and the limitation with respect to partial separation), which effectively inhibit undesirable reactions of or between the mixture's components (e.g., polymerization of olefin, reversion of alkanol to olefin, and formation or decomposition of heavy by-product). The conditions of acididty and temperature in the second evaporation step are designed to essentially complete the evaporative recovery of alkanol and olefin remaining in the bottoms liquid of the first step, while at the same time promoting decomposition of heavy by-product into recoverable alkanol and olefin. The acid wash step first releases alkanol from the alkoxide form in which it is in part held as the result of the requirement for alkaline conditions in the first evaporation, and also reconverts alkyl sulfate and sulfonate by-product components into their less stable acidic forms. For the invention to accomplish improvement in process selectivity, it is essential that, before decomposition of heavy by-product is attempted, the first evaporation step be carried out for removal therefrom of a substantial portion of alkanol and olefin. Otherwise the advantages of the alkanol and olefin recovery from by-product are offset or outweighed by their consumption in side reactions, thus decreasing process selectivity, or in reverse of alkanol to olefin, substantially decreasing process yield.

Temperature of the liquid in the second evaporation step necessarily reaches at least about 400° F. Preferably, the evaporation is continuously carried out at or, in the case of batch operation taken to, a temperature in the range from about 425° to 500° F., while a temperature in the range from about 435° to 475° F. is considered more preferred and a temperature of about 445° to 450° F. most preferred. Evaporation pressure will be the vapor pressure of the evaporation liquid, i.e., the bottoms liquid, at the temperature chosen. In order to maximize recovery of alkanol and olefin, both that present in the feed to this evaporation step and that generated by decomposition reactions, evaporation under vacuum is preferred, especially in the processing of alkanols of relatively high carbon number, e.g., $C_{14}$ to $C_{20}$. It is also preferable that the liquid in the second evaporation step be subjected to the specified temperature for an extended time. For instance, a residence time for the liquid at such a temperature of greater than about 15 minutes is particularly preferred, and liquid residence times of at least about 30 minutes are still more preferred and residence times in excess of one hour most preferred.

Liquid in the second evaporation is preferably continuously circulated to prevent fouling of heat exchange and other equipment surfaces with which it is in contact.

The invention, and specifically certain of its preferred embodiments, are described in the following Examples. Comparative Examples are also presented.

EXAMPLE

Under the process flow scheme described above with reference to the drawing, the invention is applied to a crude alkanol reaction mixture derived from mixed $C_{13}$ and $C_{14}$ predominantly linear olefins via sulfation and hydrolysis reactions. These reactions are carried out in accordance with procedures described in the examples of the above-referenced application, Ser. No. 363,175. With flowrates in terms of pound-equivalents of alkyl group per hour (lb-eq/hr), the crude reaction mixture contains about 9.0 lb-eq/hr of $C_{13}$ and $C_{14}$ olefin, about 37.7 lb-eq/hr $C_{13}$ and $C_{14}$ alkanol, and about 3.3 lb-eq/hr heavy by-product, for a total of about 50 lb-eq/hr. This crude alkanol is mixed with the overhead vapor of the second evaporation step (containing about 2.1 lb-eq/hr $C_{13}/C_{14}$ olefin, 3.3 lb-eq/hr $C_{13}/C_{14}$ alkanol and 0.6 lb-eq/hr heavy by-product) and also with a quantity of a 50%w aqueous caustic solution. Evaporation of the resulting alkaline mixture at about 35 mmHg and 345° F. yields a first evaporation overhead vapor (about 11.1 lb-eq/hr of $C_{13}/C_{14}$ olefin, 36.9 lb-eq/hr of $C_{13}/C_{14}$ alkanol, and 0.3 lb-eq/hr of heavy by-product) which is withdrawn from the process as shown and a first evaporation bottoms liquid (about 0.3 lb-eq/hr of $C_{13}/C_{14}$ olefin, 3.7 lb-eq/hr of $C_{13}/C_{14}$ alkanol, and about 3.6 lb-eq/hr heavy by-product). Addition of the aqueous caustic to the crude reaction mixture is sufficient to give the bottoms liquid a pH between about 9 and 12. To the approximately 7.6 lb-eq/hr of bottoms liquid is added an equal weight of dilute aqueous acid (3%w $H_2SO_4$) for the acid wash step. The resulting mixture is stirred at a temperature of 212° F. for an average of 30 minutes and then allowed to phase separate into an upper organic contact phase and a lower aqueous contact effluent. In the second evaporation step, the organic contact phase is subjected to a temperature of about 450° F. and a pressure of about 35 mmHg to produce the second evaporation overhead vapor, described above, and the second evaporation bottoms liquid (about 1.6 lb-eq/hr heavy by-product together with a trace amount (e.g., less than 0.1 lb-eq/hr) of alkanol and olefin). Average residence time of bottoms liquid in the second evaporation step is about 4 hours.

Overall, the invention accomplishes a roughly 40% reduction in heavy by-product from the 3.3 lb-eq/hr of the crude alkanol reaction mixture to the total of 1.9 lb-eq/hr in the alkanol and olefin rich first evaporation overhead vapor (containing about 0.3 lb-eq/hr heavy by-product) and in the second evaporation bottoms liquid (about 1.6 lb-eq/hr heavy by-product). There is a corresponding increase in recovered $C_{13}/C_{14}$ product alkanol and $C_{13}/C_{14}$ olefin.

COMPARATIVE EXAMPLES

Comparison can be made of the results of the above Example of the invention with a process in which both the first and second evaporations are carried out under alkaline pH.

The procedures of the Example are again followed for treatment of the same crude reaction mixture, although in this comparative example the first evaporation bottoms 17 is routed directly to the second evaporation step, in the place of stream 31, omitting the acid wash step. The second evaporation step is then conducted under alkaline pH, again at 35 mmHg, 450° F., and with a bottoms liquid residence time of 4 hours. Process flows, in pound-equivalents of alkyl group per hour, are as follows:

| first evaporation overhead vapor | |
| --- | --- |
| olefin | 9.4 |
| alkanol | 37.2 |
| heavy by-product | 0.3 |
| first evaporation bottoms liquid | |
| olefin | 0.3 |
| alkanol | 3.8 |
| heavy by-product | 3.6 |
| second evaporation bottoms liquid | |
| olefin | 0.0 |
| alkanol | 0.1 |
| heavy by-product | 3.0 |
| second evaporation overhead vapor | |
| olefin | 0.4 |
| alkanol | 3.6 |
| heavy by-product | 0.6 |

This comparative example results in no net reduction of heavy by-product—the total quantity in the first evaporator overhead (0.3 lb-eq/hr) and in the second evaporator bottoms (3.0 lb-eq/hr) is essentially the same as that in the crude alkanol reaction mixture (3.3 lb-eq/hr). Overall yield of alkanol in the first evaporation overhead is only about 0.8% (0.3 lb-eq/hr) greater than under the invention, while selectivity in the process as a whole, taking into account recycle of olefin, is approximately 3% less.

Under another processing alternative (again not in accordance with the invention) alkanol and olefin could be recovered by direct evaporation of the acidic crude alkanol mixture. Essentially complete removal of alkanol and olefin could be accomplished, together with heavy by-product decomposition, in one or more evaporation steps, each of which is conducted under acidic pH. However, the results of the above example of the invention illustrate that a meaningful decomposition of heavy by-product is then achieved only with substantial sacrifice in alkanol yield. In the second (acidic) evaporation step of the example, a loss of approximately ten percent of alkanol introduced via stream 31 is acceptable because the total alkanol in 31 is only about ten percent of that in the total crude reaction mixture. Overall yield loss of alkanol during evaporation, calculated on alkanol in the crude reaction mixture, is thus on the order of one percent (i.e., ten percent of ten percent). It is apparent, however, that subjecting the entire crude reaction mixture to evaporation under acidic conditions in order to decompose a significant amount of heavy by-product, (without prior removal of alkanol under an alkaline first evaporation) would result in an approximately ten fold greater yield loss.

We claim as our invention:

1. In the process for the preparation of a $C_6$ to $C_{20}$ alkanol which comprises sulfating a $C_6$ to $C_{20}$ olefin starting material, hydrolyzing resulting alkylsulfuric acids to obtain a crude alkanol reaction mixture containing $C_6$ to $C_{20}$ alkanol together with $C_6$ to $C_{20}$ olefin starting material and heavy by-product, and separating the crude alkanol reaction mixture into alkanol and olefin rich vapor and heavy by-product rich liquid, the improvement in separation of alkanol and olefin from the crude alkanol reaction mixture which comprises:
   (a) in a first evaporation step, evaporating the crude reaction mixture under alkaline pH, withdrawing an alkanol and olefin rich first evaporation overhead vapor containing between about 80 and 98 percent by weight of the alkanol present in the crude reaction mixture and withdrawing a first evaporation bottoms liquid,
   (b) in an acid wash step, contacting the first evaporation bottoms liquid with an aqueous acid contact solution, withdrawing a washed organic contact phase, and withdrawing an aqueous contact effluent phase, with the provision that the acid content of the aqueous acid contact solution is sufficient to result in the aqueous contact effluent phase having a pH less than about 1.5, and
   (c) in a second evaporation step, evaporating the washed organic contact phase under acidic pH, at a temperature of at least 400° F., withdrawing a heavy by-product rich second evaporation bottoms liquid, with the provision that the average residence time of the second evaporation bottoms liquid at the temperature of the second evaporation is at least about 15 minutes, and withdrawing an alkanol and olefin rich second evaporation overhead vapor, said second evaporation overhead vapor containing a combined quantity by mole of alkanol and olefin greater than that contained in the washed organic contact phase.

2. The process of claim 1, wherein the second evaporation overhead vapor is recycled for evaporation together with the crude reaction mixture in the first evaporation step.

3. The process of claim 2, wherein the acid content of the aqueous contact solution is sufficient to result in the aqueous contact effluent phase having a pH between about 0.0 and 1.0.

4. The process of claim 3, wherein the temperature of the first evaporation step is less than 400° F. and the temperature in the second evaporation step is at least 400° F.

5. The process of claim 5, wherein the first evaporation overhead vapor contains between about 85 and 96 percent by weight and the first evaporation bottoms liquids contains at least 4 percent by weight of the alkanol present in the crude reaction mixture.

6. The process of claim 5, wherein the olefin starting material and alkanol product are in the $C_8$ to $C_{18}$ range.

7. The process of claim 6, wherein the first and second evaporation steps are carried out under vacuum.

8. The process of claim 7, wherein the average residence time of the second evaporation bottoms liquid at a temperature between about 425° F. and 500° F. is at least about 30 minutes.

9. The process of claim 8, wherein the first evaporation bottoms liquid has a pH between about 8 and 13.

10. In the process for the preparation of a $C_9$ to $C_{16}$ alkanol which comprises sulfating a $C_9$ to $C_{16}$ olefin starting material, hydrolyzing resulting alkylsulfuric acids to obtain a crude alkanol reaction mixture containing $C_9$ to $C_{16}$ alkanol together with $C_9$ to $C_{16}$ olefin starting material and heavy by-product, and separating the crude alkanol reaction mixture into alkanol and olefin rich vapor and heavy by-product rich liquid, the improvement in separation of alkanol and olefin from the crude alkanol reaction mixture which comprises:
   (a) in a first evaporation step, evaporating the crude alkanol reaction mixture under alkaline pH at a temperature in the range from about 330° to 360° F. and at a pressure less than about 50 mmHg, withdrawing an alkanol and olefin rich first evaporation overhead vapor containing between about 90 and 95 percent by weight of the alkanol present in the crude reaction mixture and withdrawing a first evaporation bottoms liquid containing at least 5 percent by weight of the alkanol present in the crude reaction mixture,
   (b) in an acid wash step, contacting the first evaporation bottoms liquid with a volume of an aqueous sulfuric acid contact solution that is between about 0.2 and 10 times the volume of said bottoms liquid, withdrawing a washed organic contact phase and withdrawing an aqueous contact effluent phase, with the provision that the acidity of the aqueous acid contact solution is sufficient to result in the aqueous contact effluent phase having a pH between about 0.3 and 0.7,
   (c) in a second evaporation step, evaporating the washed organic contact phase under acidic pH at a temperature in the range from about 435° F. to 475° F. and at a pressure less than about 50 mmHg, withdrawing a heavy by-product rich second evaporation bottoms liquid, with the provision that the average residence time of the second evaporation bottoms liquid at a temperature in the range from about 435° to 475° F. is at least about 30 minutes, and withdrawing an alkanol and olefin rich second evaporation overhead vapor, said second evaporation overhead vapor containing a combined quantity by mole of alkanol and olefin greater than that contained in the washed organic contact phase, and
   (d) recycling at least a portion of the second evaporation overhead vapor to the first evaporation step.

* * * * *